(12) United States Patent
Zimmerman et al.

(10) Patent No.: US 9,656,053 B2
(45) Date of Patent: May 23, 2017

(54) MEDICAL LEAD SYSTEM WITH ROUTER

(75) Inventors: James A. Zimmerman, Blaine, MN (US); Jason D. Rahn, Andover, MN (US)

(73) Assignee: MEDTRONIC, INC., Minneapolis, MN (US)

(*) Notice: Subject to any disclaimer, the term of this patent is extended or adjusted under 35 U.S.C. 154(b) by 640 days.

(21) Appl. No.: 12/900,843

(22) Filed: Oct. 8, 2010

(65) Prior Publication Data
US 2011/0087305 A1    Apr. 14, 2011

Related U.S. Application Data

(60) Provisional application No. 61/250,493, filed on Oct. 9, 2009.

(51) Int. Cl.
*A61N 1/08* (2006.01)
*A61N 1/05* (2006.01)

(52) U.S. Cl.
CPC ............. *A61N 1/05* (2013.01); *A61N 1/0553* (2013.01)

(58) Field of Classification Search
USPC ...... 607/55–57, 59, 66, 70, 72, 73, 115–118
See application file for complete search history.

(56) References Cited

U.S. PATENT DOCUMENTS

| | | | |
|---|---|---|---|
| 5,328,442 A | 7/1994 | Levine | |
| 6,847,845 B2 | 1/2005 | Belden | |
| 6,876,885 B2 | 4/2005 | Swoyer et al. | |
| 6,937,897 B2 | 8/2005 | Min et al. | |
| 2008/0046023 A1* | 2/2008 | Fischell | 607/45 |
| 2008/0154340 A1* | 6/2008 | Goetz et al. | 607/59 |
| 2008/0177366 A1* | 7/2008 | Bolea | A61N 1/05 607/118 |
| 2008/0200973 A1* | 8/2008 | Mallozzi et al. | 607/142 |

* cited by examiner

*Primary Examiner* — Erica Lee
(74) *Attorney, Agent, or Firm* — Mueting, Raasch & Gebhardt, P.A.

(57) ABSTRACT

A medical electrical lead system includes an electrical signal generator providing a plurality of discrete electrical signal channels and an electrical signal channel router electrically coupled between the electrical signal generator and a first lead body and a second lead body. The electrical signal channel router diverts one of the discrete electrical signal channels to the second lead body and not to the first lead body.

20 Claims, 3 Drawing Sheets

MEDICAL LEAD SYSTEM WITH ROUTER

RELATED APPLICATIONS

This application claims priority to U.S. Provisional Patent Application Ser. No. 61/250,493, filed on Oct. 9, 2009 and titled "MEDICAL LEAD SYSTEM WITH ROUTER". The entire disclosure of U.S. Provisional Patent Application Ser. No. 61/250,493 is incorporated herein by reference.

BACKGROUND

Many implantable medical devices, such as neurostimulators, pacemakers and defibrillators, transmit electrical signals to provide therapy to a patient. Implantable medical leads deliver signals generated from such devices to tissue of the patient via one or more electrodes of the lead. Often the electrodes of the leads are located at a considerable distance from the implant location of the electrical signal generator device. If multiple leads are required or desired, separate subcutaneous paths may need to be tunneled for, each lead, resulting in time consuming surgical procedures and patient discomfort.

In some situations a lead extension is employed to couple the lead to the signal generator. The lead extension may allow for connection of the lead in closer proximity to the tissue to which the generated electrical signal is applied, reducing the extent of tunneling required for the lead. However, the extension needs to be tunneled through the patient.

When it is desired to implant two leads in the same general tissue location, a bifurcated lead extension with a single proximal leg may be employed. In such cases, one tunneling path may be made from the implant location of the electrical signal generation to a location close to the target tissue for the lead extension. The two leads may then be coupled to the extension at this location and may traverse relative short distances in the patient.

However, if more than two leads are desired, a single bifurcated extension is not sufficient and more than one extended subcutaneous tunneling procedure may be required. Further, bifurcated lead extensions tend to be of limited flexibility in terms of functionality. For example, if a proximal end of a bifurcated lead extension has eight discrete electrical contacts for making eight discrete electrical connections with an electrical signal generator, the bifurcated distal end will have two separate lead receptacles, each having four internal contacts for making electrical connections with four discrete contacts of a lead.

BRIEF SUMMARY

The present disclosure relates to a medical lead system with a router. In particular, the present disclosure relates to a medical lead system with a router that directs one or more signal channels away from one lead body to a second lead body. The medical lead system with a router increases the possible electrical signal coverage across a therapeutic region without increasing the number of signal generators.

In one illustrative embodiment, a medical electrical lead system includes an electrical signal generator providing a plurality of discrete electrical signal channels and an electrical signal channel router electrically coupled between the electrical signal generator and a first lead body and a second lead body. The electrical signal channel router diverts one of the discrete electrical signal channels to the second lead body and not to the first lead body.

These and various other features and advantages will be apparent from a reading of the following detailed description.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
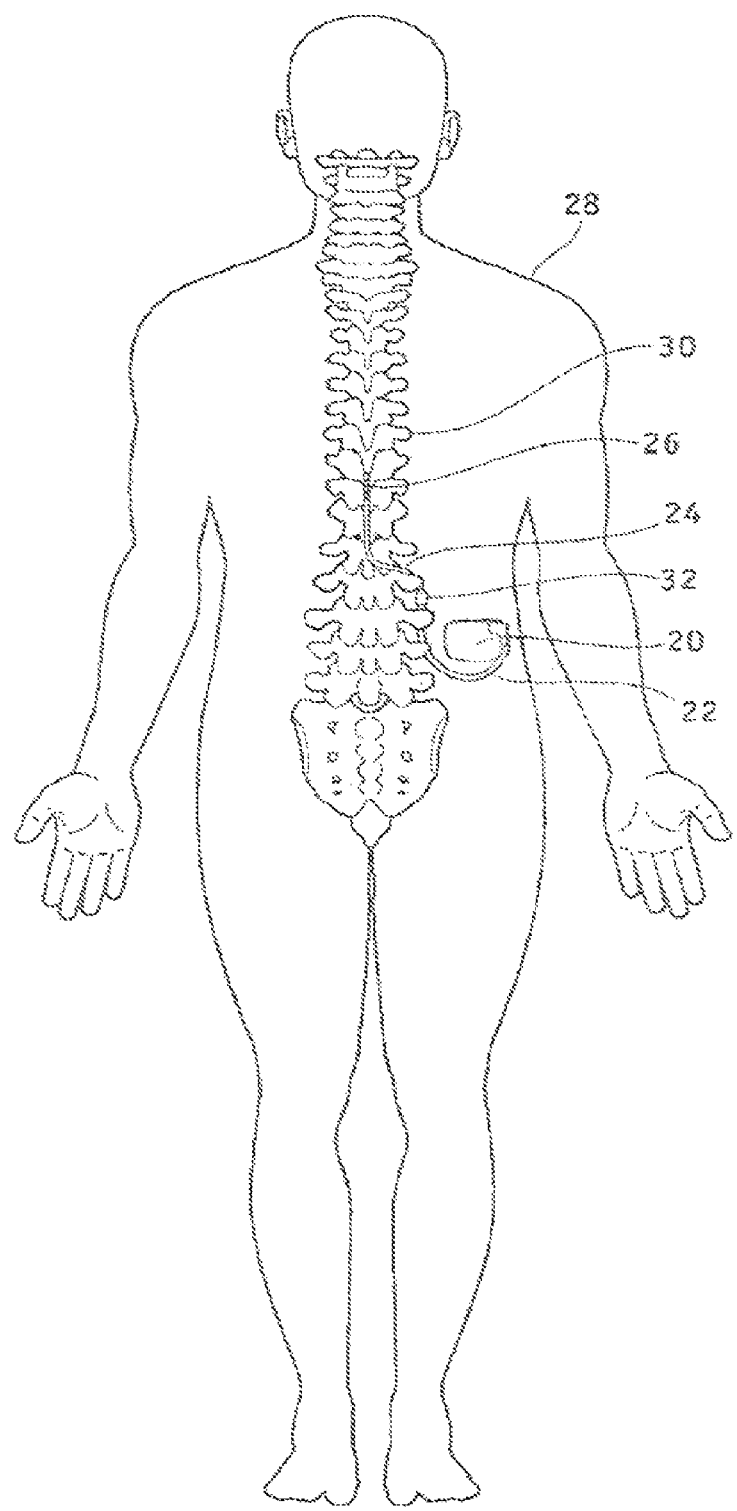
FIG. 1 is a schematic diagram of an active medical device implanted within a human body.

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "lower", "upper", "beneath", "below", "above", and "on top", if used herein, are utilized for ease of description to describe spatial relationships of an element(s) to another. Such spatially related terms encompass different orientations of the device in use or operation in addition to the particular orientations depicted in the figures and described herein. For example, if an element depicted in the figures is turned over or flipped over, portions previously described as below or beneath other elements would then be above those other elements.

As used herein, when an element, component or layer for example is described as being "on", "connected to", "coupled with" or "in contact with" another element, component or layer, it can be directly on, directly connected to, directly coupled with, in direct contact with, or intervening elements, components or layers may be on, connected, coupled or in contact with the particular element, component or layer, for example. When an element, component or layer for example is referred to as "directly on", "directly connected to", "directly coupled with", or "directly in contact with" another element, there are no intervening elements, components or layers for example.

The present disclosure relates to a medical lead system with a router. In particular the present disclosure relates to a medical lead system with a router that directs one or more signal channels away from one lead body to a second lead body. The medical lead system with a router increases the possible electrical signal coverage across a therapeutic region without increasing the number of signal generators. While the present disclosure is not so limited, an appreciation of various aspects of the disclosure will be gained through a discussion of the examples provided below.

The teachings presented herein are applicable to any implantable medical device system employing leads for delivering electrical signals to a tissue of a patient. For example, the system may include a neurostimulator, such as a peripheral nerve stimulator, a spinal cord stimulator, or a deep brain stimulator; a cardiac pacemaker or defibrillator; a gastric stimulator; or the like. It will be understood that the systems and devices described herein may be readily applied to systems employing leads for purposes of screening, sensing, monitoring, recording, or the like.

FIG. 1 is a schematic diagram of an active medical device 20 implanted within a human body or patient 28. The implanted active medical device 20 is illustrated as a neurostimulator; however, the implanted active medical device 20 can be any "active implantable medical device" or "implantable signal generator" as described above and can be placed in any location within a body cavity or tissue within the body, or on the surface of a patient's skin, as desired.

The illustrated active medical device 20 is coupled to a lead extension 22 having a proximal end coupled to the active medical device 20, and a lead 24 having a proximal end coupled to a distal end 32 of the lead extension 22 and a distal end of the lead 24 coupled to one or more electrodes 26. In other embodiments, the lead 24 proximal end is coupled to the active medical device 20, without a need for a lead extension 22. The active medical device 20 can be implanted in any useful region of the body such as in the abdomen of a patient 28, and the lead 24 is shown placed somewhere along the spinal cord 30 (e.g., a midline spinal configuration). In many embodiments, the active medical device 20 has one or two leads, each having four to eight electrodes. Such a system may also include a physician programmer and a patient programmer (not shown). The active medical device 20 can be considered to be an implantable signal generator of the type available from Medtronic, Inc. and capable of generating multiple signals occurring either simultaneously or one signal shifting in time with respect to the other, and having independently varying amplitudes and signal widths. The active medical device 20 contains a power source and the electronics for sending precise, electrical signals to the patent to provide the desired treatment therapy. While the active medical device 20, in many embodiments, provides electrical stimulation by way of signals, other forms of stimulation may be used as continuous electrical stimulation.

In many embodiments, the lead 24 is a wire having insulation thereon and includes one or more insulated electrical conductors each coupled at their proximal end to a connector and to contacts/electrodes 26 at its distal end. Some leads are designed to be inserted into a patient percutaneously (e.g. the Model 3487A Pisces—Quad® lead available from Medtronic, Inc.), and some are designed to be surgically implanted (e.g. Model 3998 Specify® lead, also available from Medtronic, Inc.). In some embodiments, the lead 24 may contain a paddle at its distal end for housing electrodes 26. In many embodiments, electrodes 26 may include one or more ring contacts at the distal end of lead 24.

Figure 2:
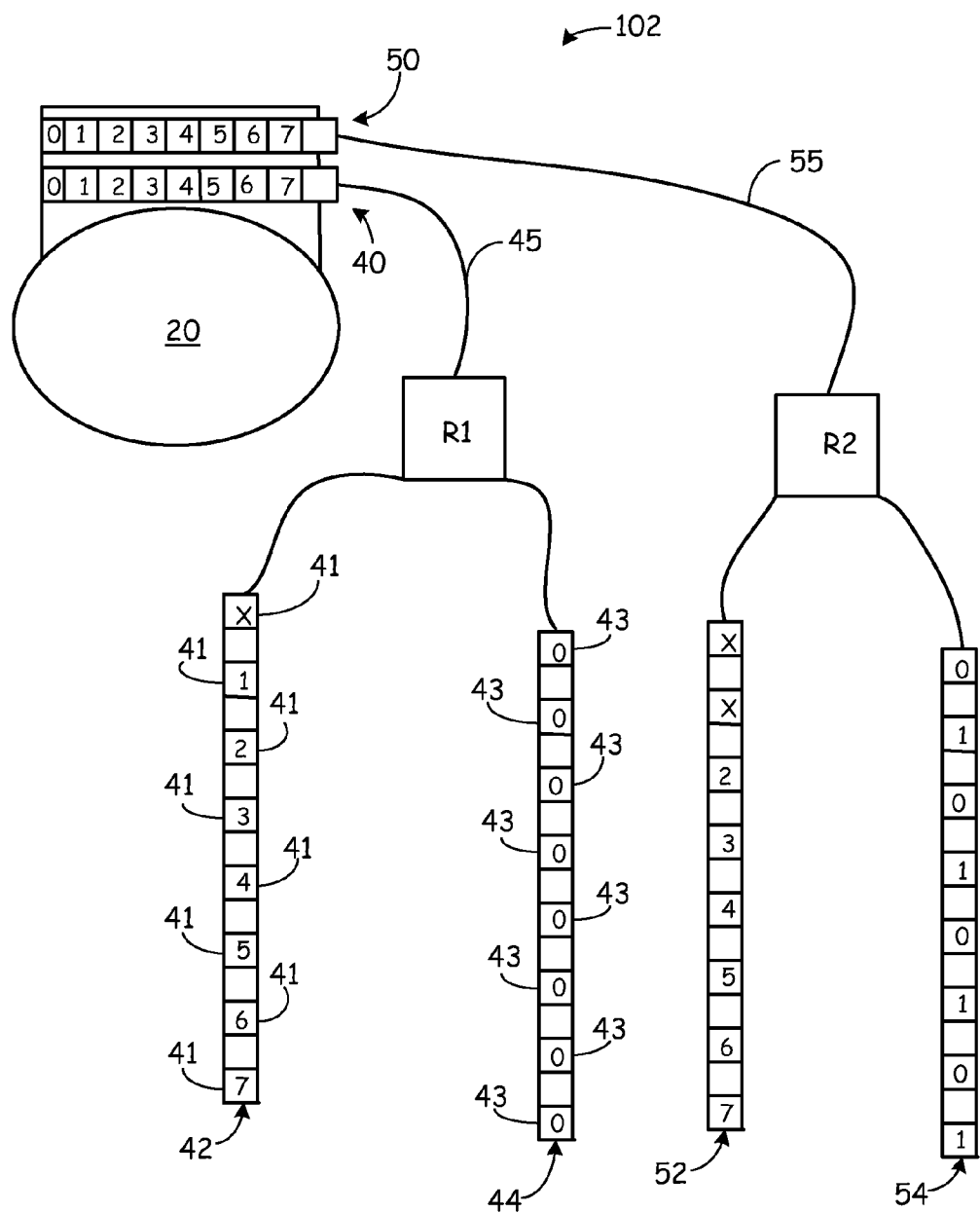
FIG. 2 is a schematic diagram view of a medical lead system with router.
Figure 3:
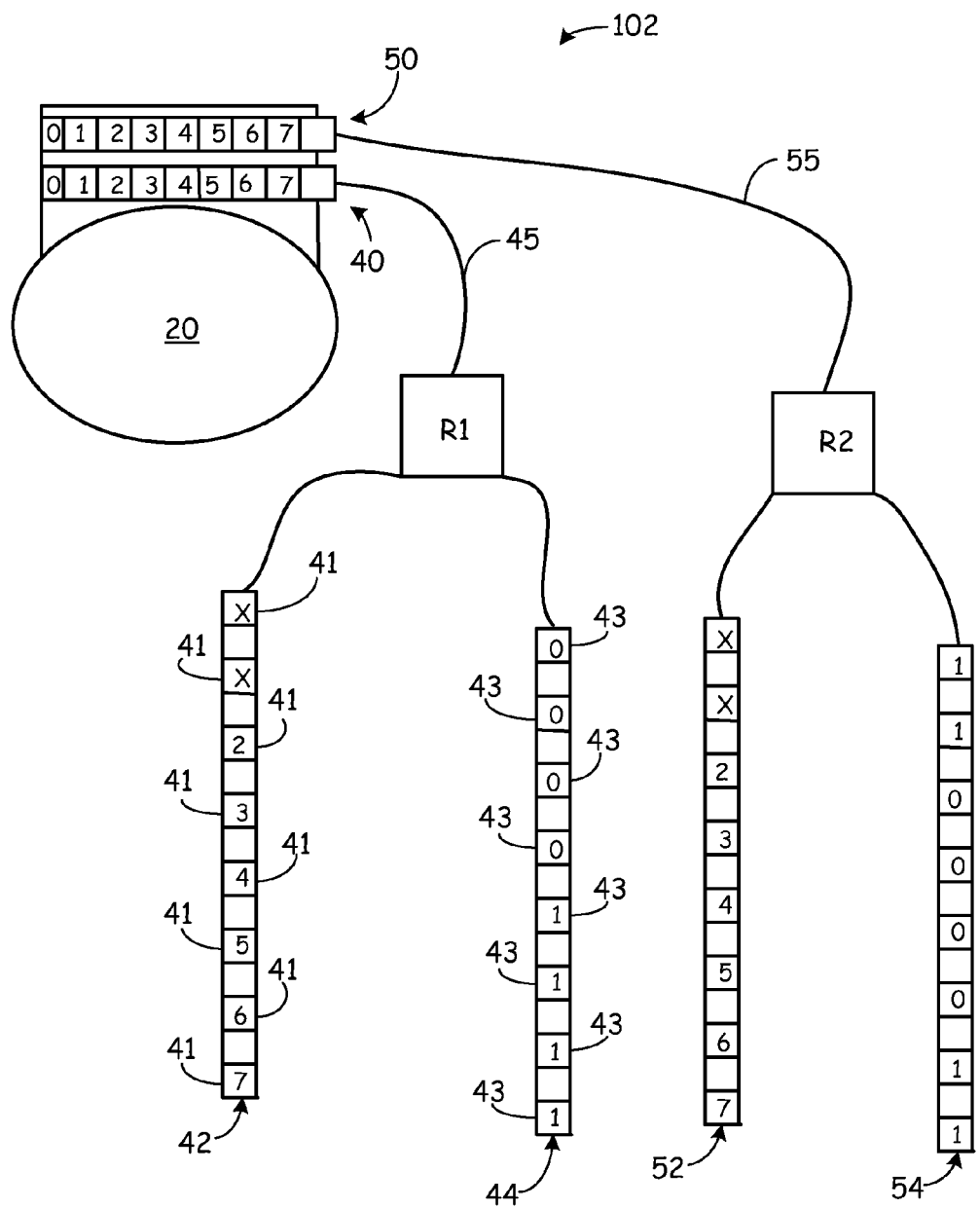
FIG. 3 is a schematic diagram view of another medical lead system with router.

FIG. 2 is a schematic diagram view of a medical lead system 102. FIG. 3 is a schematic diagram view of another medical lead system 102. The medical electrical lead system 102 includes an electrical signal generator 20 providing a plurality of discrete electrical signal channels 0, 1, 2, 3, 4, 5, 6, 7. While eight discrete electrical signal channels are illustrated, it is understood that the electrical signal generator 20 can provide any useful number of discrete electrical signal channels such as 2, 4, 6, 10, 12, 14, or 16, for example.

An electrical signal channel router R1 is electrically coupled between the electrical signal generator 20 and a first lead body 42 and a second lead body 44. In FIG. 2, the electrical signal channel router R1 diverts one of the discrete electrical signal channels (channel 0) to the second lead body 44 and not to the first lead body 42. In other words, channel 0 is directed to the second lead body 44 and not to the first lead body 42. In FIG. 3, the electrical signal channel router R1 diverts two of the discrete electrical signal channels (channel 0, 1) to the second lead body 44 and not to the first lead body 42. In other words, channel 0, 1 are directed to the second lead body 44 and not to the first lead body 42.

A lead connector 40 electrically connects the electrical signal generator 20 and a lead 45. The lead 45 electrically connects the lead connector 40 to the electrical signal channel router R1. The lead connector 40 includes a plurality of electrical contacts that electrically connect with each of the plurality of discrete electrical signal channels 0, 1, 2, 3, 4, 5, 6, 7 as illustrated. While a second lead connector 50 is illustrated, it is understood that the medical lead system 102 can include only a single lead connector or more than two lead connectors, as desired.

In many embodiments the first lead body 42 and a second lead body 44 include a plurality of electrical contact regions 41 and 43 respectively. The electrical signal channel router R1 diverts at least one of the discrete electrical signal channels (channel 0 in FIG. 2 and channels 0 and 1 in FIG. 3) to two or more of the second lead body 44 plurality of electrical contact regions 43. In FIG. 2 the electrical signal channel router R1 diverts one of the discrete electrical signal channels (channel 0) to all (i.e., eight) of the second lead body 44 plurality of electrical contact regions 43. In FIG. 2 the diverted discrete electrical signal channel (channel 0) is not applied to the first lead body 42 electrical contact regions 41.

In FIG. 3 the electrical signal channel router R1 diverts two of the discrete electrical signal channels (channel 0 and 1) to all (i.e., eight) of the second lead body 44 plurality of electrical contact regions 43. In FIG. 3 the diverted discrete electrical signal channels (channel 0 and 1) are not applied to the first lead body 42 electrical contact regions 41. In FIG. 3 channel 0 is applied to the first four proximal contact regions 43 (sequentially) and the channel 1 is applied to the last four distal contact regions 43 (sequentially). Thus, channel 0 is applied to a first half (or proximal end half) of the second lead body 44 and channel 1 is applied to a second half (or distal end half) of the second lead body 44.

The electrical signal channel router R1 expands the electrical coverage that a single electrical signal generator 20 can provide. For example, the first lead body 42 can be implanted along a spinal cord of a patient and the second lead body 44 can be placed along a lower back region of a patient.

In some embodiments the medical electrical lead system 102 includes a second electrical signal channel router R2. The second electrical signal channel router R2 can divert the same or different channels between two lead bodies 52, 54 as R1 does for the first two lead bodies 42, 44. In FIG. 2 the electrical signal channel router R2 diverts two of the discrete electrical signal channels (channel 0 and channel 1) to the second lead body 54 and not to the first lead body 52. In other words, channel 0 and channel 1 is directed to the second lead body 54 and not to the first lead body 52.

The first lead body 52 and a second lead body 54 include a plurality of electrical contact regions. In FIG. 2 the electrical signal channel router R2 diverts two of the discrete electrical signal channels (channel 0 and channel 1) to three or more of the second lead body 54 plurality of electrical contact regions.

The two discrete electrical signal channels can be applied to the second lead body 54 plurality of electrical contact regions in any manner desired. In FIG. 2 the illustrated example provides the two of the discrete electrical signal channels (channel 0 and channel 1 in this illustrated embodiment) to alternating electrical contact regions of the second lead body 54. In other embodiments the first discrete electrical signal channel can be applied to a plurality of adjacent electrical contact regions of the second lead body 54 and the second discrete electrical signal channel can be applied to the remaining electrical contact regions of the second lead body 54.

In FIG. 3 the electrical signal channel router R2 diverts two of the discrete electrical signal channels (channel 0 and 1) to all (i.e., eight) of the second lead body 54 plurality of electrical contact regions. In FIG. 3 the diverted discrete electrical signal channels (channel 0 and 1) are not applied to the first lead body 52 electrical contact regions. In FIG. 3 channel 0 is applied to the four contact regions located closest to the proximal and distal ends of the elongate second lead body 54 and the channel 1 is applied to the four contact regions between the proximal and distal end contact regions of the elongate second lead body 54. Thus, channel 0 is applied to a middle portion of the second lead body 54 and channel 1 is applied to end portions of the second lead body 54.

The electrical signal channel router R2 expands the electrical coverage that a single electrical signal generator 20 can provide. For example, the first lead body 52 can be implanted along a spinal cord of a patient and the second lead body 54 can be placed along a lower back region of a patient.

In some embodiments, the electrical signal channel router R1, R2 is configured to select and divert either a first discrete electrical signal channel or a second discrete electrical signal channel to two or more of the second lead body 44, 54 plurality of electrical contact regions. In other embodiments, the electrical signal channel router R1, R2 is configured to select and divert either a first discrete electrical signal channel or a second discrete electrical signal channel or a first and second discrete electrical signal channel to two or more of the second lead body 44, 54 plurality of electrical contact regions.

The illustrated medical lead system 102 includes two electrical signal channel routers R1, R2 electrically coupled to a single electrical signal generator 20, where the first electrical signal channel router R1 diverts a single discrete electrical signal channel 0 to two or more of the second lead body 44 plurality of electrical contact regions and the second electrical signal channel router R2 diverts two discrete electrical signal channel 0 and 1 to three or more of the second lead body 54 plurality of electrical contact regions. It is understood that the medical lead system 102 can include only one electrical signal channel router. It is also understood that the two electrical signal channel routers R1, R2 can both only divert one discrete electrical signal channel (that may or may not be the same discrete electrical channel) or both divert two of the same or different discrete electrical signal channels.

Thus, embodiments of the MEDICAL LEAD SYSTEM WITH ROUTER are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation, and the present invention is limited only by the claims that follow.

What is claimed is:

1. A medical electrical lead system comprising;
    an electrical signal generator providing a plurality of discrete electrical signal channels, the electrical signal generator comprising a lead connector;
    a lead electrically coupled to and received within the lead connector;
    an implantable electrical signal channel router electrically coupled between the lead and a plurality of electrical contact regions on a first lead body and on a second lead body, each of the first lead body plurality of electrical contact regions having only one corresponding discrete electrical signal channel, the electrical signal channel router being configured to:
        divert one or more of the discrete electrical signal channels to the second lead body and not to the first lead body by electrically connecting the diverted one or more discrete electrical signal channels to one or more of the second lead body plurality of electrical contact regions, wherein the first lead body plurality of electrical contact regions corresponding to the diverted discrete electrical signal channels are electrically isolated from the electrical signal generator; and
        electrically connect the remaining discrete electrical signal channels of the plurality of discrete electrical signal channels to only the corresponding first lead body plurality of electrical contact regions, wherein the remaining discrete electrical signal channels are electrically isolated from the second lead body plurality of electrical contact regions.

2. A medical electrical lead system according to claim 1, wherein the electrical signal channel router diverts at least one of the discrete electrical signal channels to two or more of the second lead body plurality of electrical contact regions.

3. A medical electrical lead system according to claim 1, wherein the electrical signal channel router diverts one of the discrete electrical signal channels to all of the second lead body plurality of electrical contact regions.

4. A medical electrical lead system according to claim 1, wherein the electrical signal channel router diverts two of the discrete electrical signal channels to the second lead body and not to the first lead body.

5. A medical electrical lead system according to claim 4, wherein the electrical signal channel router is configured to divert either a first discrete electrical signal channel or a second discrete electrical signal channel to two or more of the second lead body plurality of electrical contact regions.

6. A medical electrical lead system according to claim 4, wherein the electrical signal channel router is configured to divert either one or two discrete electrical signal channels to two or more of the second lead body plurality of electrical contact regions.

7. A medical electrical lead system according to claim 4, wherein the electrical signal channel router diverts one of the discrete electrical signal channels to proximal and distal end electrical contact regions on the second lead body and the electrical signal channel router diverts one of the discrete electrical signal channels to electrical contacts regions disposed between the proximal and distal end electrical contact regions.

8. A medical electrical lead system according to claim 4, wherein the electrical signal channel router diverts one of the discrete electrical signal channels to a proximal end half electrical contact regions on the second lead body and the electrical signal channel router diverts one of the discrete electrical signal channels to a distal end half electrical contacts regions on the second lead body.

9. A medical electrical lead system according to claim 1, wherein the electrical signal generator comprises a second lead connector and a second lead is received in the second lead connector and a second electrical signal channel router electrically coupled between the second lead and a third lead body and a fourth lead body, the second electrical signal channel router diverts one of the discrete electrical signal channels to the fourth lead body and not to the third lead body.

10. A medical electrical lead system comprising;
an electrical signal generator providing a plurality of discrete electrical signal channels;
a first lead connector disposed within the electrical signal generator;
a second lead connector disposed within the electrical signal generator;
a first lead electrically coupled to and received within the first lead connector;
a second lead electrically coupled to and received within the second lead connector; and
an implantable first electrical signal channel router electrically coupled between the first lead and a plurality of electrical contact regions on a first lead body and on a second lead body, each of the first lead body plurality of electrical contact regions having only one corresponding discrete electrical signal channel, wherein the first electrical signal channel router is configured to:
divert two of the discrete electrical signal channels to the second lead body and not to the first lead body by electrically connecting the diverted two discrete electrical signal channels to two or more of the second lead body plurality of electrical contact regions, wherein the first lead body plurality of electrical contact regions corresponding to the diverted discrete electrical signal channels are electrically isolated from the electrical signal generator; and
electrically connect the remaining discrete electrical signal channels of the plurality of discrete electrical signal channels to only the corresponding first lead body plurality of electrical contact regions, wherein the remaining discrete electrical signal channels are electrically isolated from the second lead body plurality of electrical contact regions.

11. A medical electrical lead system according to claim 10, wherein the first electrical signal channel router diverts two of the discrete electrical signal channels to three or more of the second lead body plurality of electrical contact regions.

12. A medical electrical lead system according to claim 10, wherein the first electrical signal channel router diverts a first discrete electrical signal channel to two of the second lead body plurality of electrical contact regions and the first electrical signal channel router diverts a second discrete electrical signal channel to two of the second lead body plurality of electrical contact regions.

13. A medical electrical lead system according to claim 10, wherein the first electrical signal channel router is configured to divert either a first discrete electrical signal channel or a second discrete electrical signal channel to two or more of the second lead body plurality of electrical contact regions.

14. A medical electrical lead system according to claim 10, wherein the first electrical signal channel router is configured to divert either one or two discrete electrical signal channels to two or more of the second lead body plurality of electrical contact regions.

15. A medical electrical lead system according to claim 10, wherein the first electrical signal channel router diverts one of the discrete electrical signal channels to proximal and distal end electrical contact regions on the second lead body and the first electrical signal channel router diverts one of the discrete electrical signal channels to electrical contact regions disposed between the proximal and distal end electrical contact regions.

16. A medical electrical lead system according to claim 10, wherein the first electrical signal channel router diverts one of the discrete electrical signal channels to proximal end half electrical contact regions on the second lead body and the first electrical signal channel router diverts one of the discrete electrical signal channels to distal end half electrical contact regions on the second lead body.

17. A medical electrical lead system according to claim 10, a wherein the second lead electrically is coupled to the electrical signal generator and a second electrical signal channel router electrically coupled between the second lead and a third lead body and a fourth lead body, the second electrical signal channel router diverts one of the discrete electrical signal channels to the fourth lead body and not to the third lead body.

18. A medical electrical lead system comprising;
an electrical signal generator providing a plurality of discrete electrical signal channels, the electrical signal generator comprising a lead connector;
a lead electrically coupled to and received within the lead connector;
an implantable electrical signal channel router electrically coupled between the lead and a plurality of electrical contact regions on a first lead body and on a second lead body, each of the first lead body plurality of electrical contact regions having only one corresponding discrete electrical signal channel, the electrical signal channel router being configured to:
divert a first discrete electrical signal channel to a first portion of the second lead body and not to the first lead body by electrically connecting the diverted first discrete electrical signal channel to one or more of the second lead body plurality of electrical contact regions, wherein the first lead body electrical contact region corresponding to the diverted first discrete electrical signal channel is electrically isolated from the electrical signal generator;

divert a second discrete electrical signal channel to a second portion of the second lead body and not to the first lead body by electrically connecting the diverted second discrete electrical signal channel to one or more of the second lead body plurality of electrical contact regions, wherein the first lead body electrical contact region corresponding to the diverted second discrete electrical signal channel is electrically isolated from the electrical signal generator; and electrically connect the remaining discrete electrical signal channels of the plurality of discrete electrical signal channels to only the corresponding first lead body plurality of electrical contact regions, wherein the remaining discrete electrical signal channels are electrically isolated from the second lead body plurality of electrical contact regions.

19. A medical electrical lead system according to claim 18, wherein the electrical signal channel router diverts the first discrete electrical signal channel to proximal and distal end electrical contact regions on the second lead body and the electrical signal channel router diverts the second discrete electrical signal channel to electrical contact regions disposed between the proximal and distal end electrical contact regions.

20. A medical electrical lead system according to claim 18, wherein the electrical signal channel router diverts the first discrete electrical signal channel to proximal end half electrical contact regions on the second lead body and the electrical signal channel router diverts the second discrete electrical signal channel to distal end half electrical contact regions on the second lead body.

* * * * *